United States Patent [19]

Thilly et al.

[11] Patent Number: 5,045,450
[45] Date of Patent: Sep. 3, 1991

[54] DETERMINATION OF A MUTATIONAL SPECTRUM

[75] Inventors: William G. Thilly, Winchester; Phouthone Keohavong, Cambridge, both of Mass.

[73] Assignee: Massachusetts Institute of Technology, Cambridge, Mass.

[21] Appl. No.: 379,087
[22] Filed: Jul. 13, 1989
[51] Int. Cl.$^5$ .................... C12Q 1/68; G01N 27/00
[52] U.S. Cl. ........................ 435/6; 435/91; 435/172.1; 436/501; 436/811; 536/27; 935/9; 935/10; 935/16; 935/17; 935/18; 935/19; 935/77; 935/78
[58] Field of Search .................. 435/6, 91, 172.1; 436/501, 811; 536/27; 935/9, 10, 16, 17, 18, 19, 77, 78

[56] References Cited

U.S. PATENT DOCUMENTS 4,683,202 7/1987 Mullis ..................... 435/91
4,795,699 1/1989 Tabor et al. .............. 435/5

FOREIGN PATENT DOCUMENTS

PCT/US90/-03932 7/1990 PCT Int'l Appl.

OTHER PUBLICATIONS

Olson et al., *Nucl. Acids Res.*, 2:43–60 (1975).
Kleppe, K. et al., *J. Mol. Biol.*, 56:341–361 (1971).
Mullis, K. B. et al., *Method. Enzymol.*, 155:335–350 (1987).
Saiki, R. K. et al., *Science*, 239:487–491 (1988).
Scharf, S. J. et al., *Science*, 233:1076–1078 (1986).
Saiki, R. K. et al., *Science*, 230:1350–1354 (1985).
Wrischnik, L. A. et al., *Nucl. Acids. Res.*, 15:529–541 (1987).
Wong, C. et al., *Nature*, 330:384–386 (1987).
McMahon, G. et al., *Proc. Natl. Acad. Sci. USA*, 84:4974–4978 (1987).
Noll, W. W. et al., *Proc. Natl. Acad. Sci. USA*, 84:3339–3343 (1987).
Fischer, S. G. et al., *Proc. Natl. Acad. Sci. USA*, 80:1579–1583 (1983).
Myers, R. M. et al., *Nature*, 313:495–498 (1985).
W. G. Thilly, *Carcinogenesis*, 10:511–528 (1985).
Keohavong, P. et al., *DNA*, 7:63–70 (1988).
Keohavong, P. et al., *Gene*, 71:211–216 (1988).
Cariello, N. F. et al., *Am. J. Hum. Genet.*, 42:726–734 (1988).
Sheffield et al. (1989), *Proc. Natl. Acad. Sci., USA*, vol. 86, pp. 232–236.
Myers and Maniatis, *Cold Spring Harbor Symposia on Quantitative Biology LI:* 275–284 (1986).
Cariello et al., *Am. J. Hum. Genet.*, 42:726–734 (1988).
Shenk et al., *Proc. Nat. Acad. Sci. USA*, 72:989–993 (1975).
Cariello et al., "Use of Gradient Denaturing Gels to Determine Mutational Spectrum in Human Cells", in *Mechanisms of DNA Damage and Repair*, pp. 439–452, Simiq et al. editors, 1986, Plenum (New York).
Keohavong et al., *Proc. Natl. Acad. Sci. USA*, 86:9253–9257 (1989).

*Primary Examiner*—Robert A. Wax
*Assistant Examiner*—Ardin H. Marschell
*Attorney, Agent, or Firm*—Hamilton, Brook, Smith & Reynolds

[57] ABSTRACT

A method of resolving (physically separating) mutant DNA from nonmutant DNA and a method of defining or establishing a mutational spectrum or profile of alterations present in nucleic acid sequences from a sample to be analyzed, such as a tissue or body fluid. The present method is based on the fact that it is possible, through the use of DGGE, to separate nucleic acid sequences which differ by only a single base change and on the ability to detect the separate mutant molecules.

The present invention, in another aspect, relates to a method for determining a mutational spectrum in a DNA sequence of interest present in a population of cells.

The method of the present invention is useful as a diagnostic or analytical tool in forensic science in assessing environmental and/or occupational exposures to potentially genetically toxic materials (also referred to as potential mutagens); in biotechnology, particularly in the study of the relationship between the amino acid sequence of enzymes and other biologically-active proteins or protein-containing substances and their respective functions; and in determining the effects of drugs, cosmetics and other chemicals for which toxicity data must be obtained.

7 Claims, 2 Drawing Sheets

DETERMINATION OF A MUTATIONAL SPECTRUM

FUNDING

Work described herein was supported by Grants from the U.S. National Institute for Environmental Health Sciences and the Department of Energy.

BACKGROUND OF THE INVENTION

Several methods are currently available which can be used to study point mutations in a DNA molecule. For example, it is possible to isolate a variant cell recognized by a DNA sequence of interest, such as one thought to contain a mutation, and then sequence the cloned product, using known techniques. Alternatively, DNA to be analyzed, such as tumor DNA, can be cloned, amplified and sequenced, also using known techniques. Although it is possible, using presently-available method, to study individual DNA mutations and to determine a mutational spectrum or profile or alterations in a selected DNA sequence, to do so is time-consuming and tedious. This is due at least in part to the fact that a large number of mutants, each of which must be isolated one at a time, must be analyzed in order to get a statistically reproducible spectrum. For example, it is reasonable to assume that approximately 10 mutants per base pair (bp) of DNA sequence is necessary to give a statistically reproducible result. Thus, in the case in which the mutational spectrum of a 100 bp DNA sequence is to be determined, approximately 1000 mutants must be assessed. Using presently-available methods, each assessment requires considerable time (e.g., 1 day per mutant analyzed) and, thus, carrying out the 1000 assessments needed for a 100 bp DNA sequence is work-intensive.

In addition, presently-available methods are limited to cases in which a particular mutation is present in the germ cell of an individual or other cases in which the frequency of a particular mutation is relatively high (e.g., exceeding 0.1%). A method which would facilitate the detection of point mutations occurring at much lower frequencies, such as occur in nature, would be extremely valuable, particularly in situations such as those in which exposure to a toxic substance results in a useful diagnostic set of alterations or single base changes in genetic material.

SUMMARY OF THE INVENTION

The present invention pertains to a method of resolving (i.e., physically separating) mutant DNA of known sequence from nonmutant DNA and of determining or establishing a mutational spectrum, which is a profile or pattern of alterations present in DNA from a selected source, such as cells from a selected organ or a blood sample. In particular, the present method is useful for separating and identifying selected mutant DNA sequences from a complex mixed DNA population which contains the selected or target mutant DNA sequence(s), mutant DNA sequences other than the selected mutant DNA sequences and non-mutant DNA sequences. The method of the present invention has far greater sensitivity (i.e., is able to resolve mutants present at a much lower frequency) than previously-available methods. Using the method of the present invention, 100 mutant nucleotide sequences among 100,000,000 nonmutant nucleotide sequences have been resolved and, based on subsequent observations in human cell experiments, it appears to have a resolving power of at least 100 times greater (i.e., 100 mutant DNA sequences in 10,000,000,000 nonmutant DNA sequences). The subject method makes it possible to resolve DNA in those contexts in which the mutational frequency is approximately 1 to $1 \times 10^{-8}$ and approximately 100 copies of selected mutant DNA sequence, referred to as a target DNA sequence, occur in the sample being analyzed.

As a result, it is possible to resolve mutant DNA sequences and establish mutational spectra in a cell population drawn directly from human or other animal tissue. In the method of the present invention, mutant DNA sequences are those which differ by one or more nucleotides from the corresponding naturally-occurring, unaltered DNA sequence. These differences include nucleotide modifications, deletions, substitutions or insertions. The present invention further pertains to a method of identifying one or more mutations (i.e., alterations or changes from the corresponding naturally-occurring) which confer a selective advantage or disadvantage on cells in which the mutations(s) is present.

DNA to be analyzed is isolated from cells in which it occurs, is processed, if needed, in such a manner as to make it accessible to restriction endonucleases or other agent capable of cutting the DNA in a sequence specific manner and cut with one or more appropriately-selected restriction endonucleases or other sequence-specific agent to produce DNA fragments. Optionally, the resulting mixture of fragments of varying sizes can be separated or fractionated on the basis of molecular weight, using known techniques, and fragments of appropriate predetermined size are selected. The resulting digestion products or fragments are boiled and cooled under controlled conditions to allow nonmutant molecules and mutant molecules to form heteroduplexes. The mixture of fragments (or the fragments selected on the basis of size if the optional separation step is carried out) is separated into heteroduplexes and homoduplexes by means of denaturing gradient gel electrophoresis, (DGGE), which results in an initial separation of most (e.g., 99% or more) of the nonmutant (wild type or normal) DNA in the total DNA from the mutant DNA). The heteroduplexes obtained, which include mutant-containing and nonmutant complexes, are used for further assessment according to the present method and determination of the mutational spectrum. The profile or pattern of mutations in heteroduplexes which are mutant-containing can be established by making the mutations "visible" (detectable) by means of high fidelity, DNA amplification followed by a second separation of heteroduplexes from homoduplexes using DGGE and sequence determination; use of appropriately-labeled probes (e.g., fluorophore-labeled or isotopically-labeled wild type DNA) and a detection means capable of detecting and recording the label used; or other known techniques.

In another aspect, the present invention is a method of defining or establishing a mutational spectrum in a DNA sequence of interest present in a population of cells. A mutation to be detected can occur with a frequency as low as $1 \times 10^{-8}$, given that at least $10^{10}$ copies of the DNA sequence of interest (i.e., a DNA sequence which includes the mutation(s) to be detected, if such mutation(s) are present). This means that it is possible to observe mutational spectra in a cell population obtained directly from human or other animal tissue or body fluids. In defining the mutational spectrum, DNA from the cells of interest is processed, mutations present in the DNA sequence of interest are identified and characterized, as described above, and the characteristics of the sample DNA (suspected of containing one or more alterations or differences from the naturally-occurring sequence) are compared with those of wild-type or unaltered DNA. The resulting pattern of differences in sequence (pattern of mutations), which may include one or many differences, is the mutational spectrum. After sufficient analysis and verification in a sufficient number of samples from the same individual, a particular pattern of mutations can be shown to be indicative of such an exposure and used as an analytical or diagnostic tool. As part of this process, normal DNA from an individual whose DNA (e.g., from a specific affected tissue or organ or tumor DNA) is to be assessed and characterized can serve as a standard against which the sequence of DNA from the abnormal or affected site can be compared in determining whether mutations exist and establishing a mutational spectrum.

The method of the present invention can be used to identify one or more mutations which confer a selective advantage or disadvantage upon cells in which the mutations are present.

The method of the present invention makes it possible to detect mutations in DNA which occur at frequencies which cannot easily be detected using presently-available techniques. The method is, therefore, particularly useful in those contexts in which minor changes or differences in nucleotide sequence, such as a point mutation or limited number of altered nucleotides, are associated with or the cause of a particular event, such as exposure to a material known or thought to be toxic or the occurrence of a particular disease. The present method can be used as a diagnostic tool in assessing results of occupational or environmental exposures to genetically toxic or harmful materials, as a diagnostic tool in a forensic context, as a means of carrying out pharmaceutical testing and as a tool in biotechnology for determining the relationship between amino acid sequence and function of proteinaceous materials, such as enzymes.

BRIEF DESCRIPTION OF THE DRAWINGS

FIG. 2 is a diagram showing (A) the melting map for the 184 bp wild-type HPRT exon 3 sequence, and (B) the positions of primers (P) used to amplify the exon 3 sequence.

DETAILED DESCRIPTION OF THE INVENTION

The present invention pertains to a method of resolving mutant nucleic acid sequences from nonmutant nucleic acid sequences and to a method of defining or establishing a mutational spectrum or profile of alterations present in nucleic acid sequences from a sample to be analyzed, such as a tissue or body fluid. The present method is based on the fact that it is possible, through the use of DGGE, to separate nucleic acid sequences which differ by only a single base change and on the ability to detect the separate mutant molecules either by increasing the number of copies by DNA amplification or by means, such as a fluorescent marker and laser excitation and fluorescence detector, sufficiently sensitive to detect mutations which occur at a low frequency.

Figure 1:
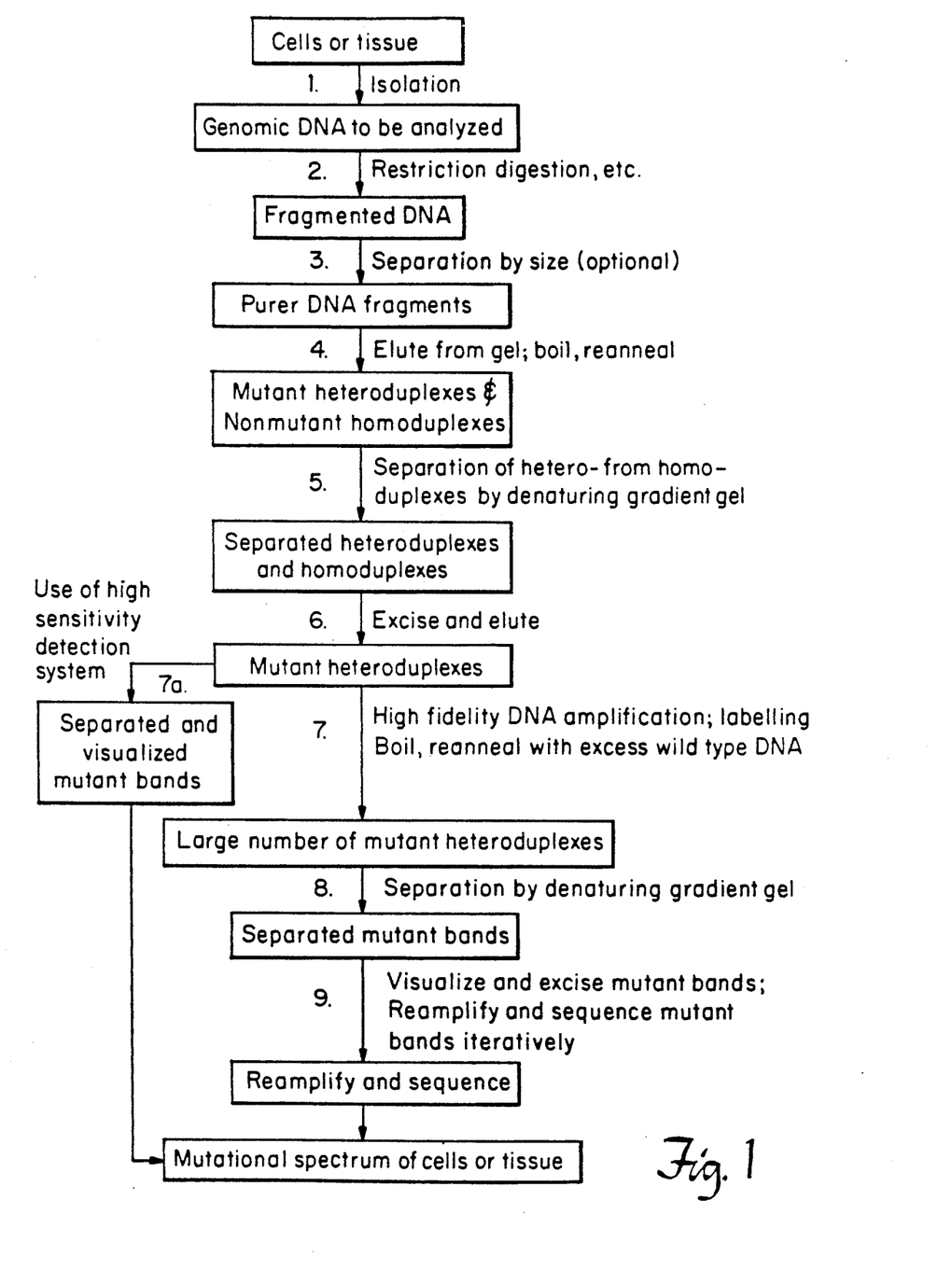
FIG. 1 is a schematic representation of the method of the present invention.

Briefly, the present method includes the following steps, which are represented schematically in FIG. 1. DNA to be analyzed for the presence of a mutant sequence or mutant sequences (DNA of interest) is obtained, using known techniques, from a tissue, body fluid or other sample (e.g., bacterium, virus, other microorganism). The number of cells needed for analysis is dependent on the particular application (particular mutation(s) to be detected) and the numbers of copies of the DNA sequence of interest (i.e., the DNA sequence to be analyzed for the presence or absence of mutation(s) present per cell. In general it is desirable to have at least 10 mutants present in the DNA sequences for each base pair in the DNA sequence of interest. In this way, it is possible to establish a sufficiently precise mutational spectrum, in which the frequency of a mutation which occurs as 1% of the total mutants present would be estimated with a standard deviation of approximately 15%.

DNA to be analyzed can be that obtained from any type of cell in which DNA is the genetic code and can be of nuclear or non-nuclear origin (e.g., from mitochondria, chloroplasts). As used herein and particularly with reference to FIG. 1, the term genomic DNA refers to any DNA constituting the hereditary material in a cell and includes all DNA in a cell, including that in organelles. For assessment of mutations in humans and other mammals. mitochondrial genes are the preferred DNA source because of the high copy number in each cell, which means that the tissue sample size required is smaller and DNA isolation is less difficult than would be the case if another DNA source were used.

DNA to be analyzed is fragmented or digested, generally by cutting with a selected restriction endonuclease(s) or other agent which can recognizably cut DNA, such as a sequence-specific chemical agent. The resulting digestion product includes fragments of varying length, only some of which include the DNA sequence in which the mutation(s) of interest, if present, occur. The fragmented DNA can, optionally, be separated initially on the basis of molecular weight to remove fragments of inappropriate size. For example, the digestion mixture can be electrophoresed through an agarose or acrylamide gel along with known molecular weight standards. The portion of the gel containing the DNA sequence of interest (and any other fragments of comparable molecular weight) can then be excised from the gel by, for example, being cut out. The DNA contained within the excised gel portion can then be purified from the gel material, for example, by electro-elution into dialysis tubing followed by ethanol precipitation.

The desired DNA fragments, or DNA fragments of interest, are selected on the basis of known DNA sequence, as well as suitability for recognition of mutants in denaturing gradient electrophoretic gels and for amplification under conditions of high fidelity, copy number and the occurrence of polymorphisms. For example, suitability for recognition in denaturing gradient electrophoretic gels is assessed by determining that a low melting domain approximately 100 to 1000 base pairs (bp) in size is in close proximity to (generally, contiguous to) a higher melting domain approximately 50 bp or more in size in such a manner that when the low melting domain of the fragment in which they occur melts on a gradient denaturing gel, the fragment has characteristically reduced mobility in the polyacrylamide electrophoretic gel. The characteristically reduced mobility is used to identify fragments containing mutant DNA. Preferably, there are also appropriately located restriction enzyme sites or other DNA sequences suitable for cleaving the mutation-containing segment (target DNA) from the isolated DNA fragment as a single DNA fragment.

As to the other criteria on which DNA fragments of interest are selected: the fragments must be suitable for high fidelity amplification because they are screened iteratively; the copy number must be sufficiently high (e.g., in genetic toxicity applications, the number of DNA sequences of interest are present at many more than 100 copies per cell); and there should be few or no genetic polymorphisms in the DNA of interest, since some inherited variation in multi copy sequences may interfere with assessment of the mutational spectrum.

The digestion product, which can be the entire mixture produced as a result of the enzymatic or chemical fragmentation of genomic DNA or a portion of the mixture selected to contain fragments of the correct size (i.e., obtained via the optional separation step), is subsequently processed to maximize formation of heteroduplex molecules. In general, this will be carried out by boiling the digestion product and allowing it to cool under controlled conditions, resulting in denaturation (separation into two strands) of the double stranded DNA and reannealing of strands to form duplexes. Nonmutant DNA forms complexes with mutant DNA, which, as a result, is uniformly present in a heteroduplex. In most contexts in which the present method is used, wild type DNA (non mutant DNA) is present in excess and heating and cooling of the digestion product can be carried out without the need for additional wild type sequences. In those instances in which this is not the case (e.g., assessment of enzyme structure) addition of wild type homoduplexes prior to boiling and reannealing may be necessary to ensure that a molar excess ($\geq 10X$) of wild type sequences is present and, thus, reduce formation of mutant:mutant duplexes.

Mutant-containing heteroduplex molecules are then separated from wild-type homoduplex molecules by denaturing gradient gel electrophoresis or other process by which double-stranded DNA fragments can be separated on the basis of a small difference in sequence. As the molecules migrate into the denaturing gradient, the heteroduplex molecules, which contain at least one mismatched base pair, melt at a lower denaturant concentration than that at which the wild-type homoduplex molecules melt. By the time the wild-type homoduplex melts, there is a significant physical separation between it and the two mutant heteroduplex pairs, which have reasonably unique (identifiable) positions on the gel. (Because of the presence in double-stranded DNA of a Watson and a Crick strand, two heteroduplexes, which can differ in the distance they move in the gel, are formed for each mutant.)

Following separation, the portion of the gel containing the wild-type homoduplex fragments is excised and discarded. The heteroduplex molecules present in the remaining gel material can be visualized (i.e., their characteristics, such as size and nucleic acid sequence, can be assessed) by one of two procedures, which are described below.

In one embodiment of the present method, as represented in FIG. 1, Steps 7-9, the DNA present in the selected heteroduplexes is amplified and visualized. Initially, the DNA in the heteroduplexes is amplified using a high fidelity DNA amplification method such as that described in co-pending U.S. patent application Ser. No. 07/065,257, the teachings of which are incorporated herein by reference. The high fidelity amplification product is boiled and cooled, to promote or maximize formation of heteroduplexes which contain mutant:nonmutant DNA sequences. In general, wild type (normal) DNA is present in sufficient quantities., in those cases in which wild type DNA is not in excess, it is added before boiling and cooling are carried out. In either case, this results in production of a greater number of mutant-containing heteroduplexes. which are a mixture of heteroduplexes (selected or target mutant DNA sequences and other mutant DNA sequences). The heteroduplexes are subjected to DGGE or other procedure capable of separating DNA fragments on the basis of a small difference in nucleic acid sequence. This results in separation among mutants, which are then individually visualized using known techniques, such as use of an isotopically labeled probe and autoradiography.

The oligonucleotide primers used in the amplification procedure (e.g.. Steps 7 and 9) can be chemically synthesized. To facilitate the identification of mutant-containing heteroduplex bands in subsequent denaturing gradient gels, the oligonucleotide primers can be labelled with a reporter group (e.g., Step 7), such as a radioactive material, using well known techniques. Such reporter groups are well known to those skilled in the art.

The primer is added to the purified DNA mixture, enriched in mutant heteroduplex molecules, in a sufficient molar excess to prime DNA synthesis efficiently. The mixture is heated to denature the mutant heteroduplexes and allowed to cool slowly.

Any of a variety of DNA polymerases can be used in the amplification protocol. These include T4 DNA polymerase (Keohavong et al., DNA, 7:63-70 (1988)); modified and unmodified T7 DNA polymerase (Keohavong et al., Gene, 71:211-216 (1988)); the Klenow fragment of DNA polymerase I (Saiki et al., Science, 230:1350-1354 (1988); Mullis et al., Methods Enzymol., 155:335-350 (1987)); and Taq DNA polymerase (Saiki et al., Science, 239:487-491 (1988)). Following amplification, amplified sequences in the amplification mixture include mutant homoduplex molecules, and wild type homoduplex molecules. The mixture is then heated and cooled under conditions appropriate for heteroduplex formation. As a result of the excess of wild-type hydrogen bonding partners, essentially all mutant-containing strands anneal with a wild-type strand to form heteroduplex molecules.

When this mixture is run on a denaturing gradient gel, a series of bands results. Homoduplex molecules migrate further in the gel and achieve greater penetration into the denaturing gradient than the bands which represent the heteroduplex molecules. For each individual mutation within the DNA sequence of interest, two labelled heteroduplex bands occur on the autoradiograph. The reason for this is that each strand of mutant homoduplex, following denaturation and annealing, forms a unique heteroduplex molecular species. Each of the two heteroduplex species melts at a characteristic temperature and the two species are resolvable by DGGE; each is a band with a characteristic location on the gel.

Individual band(s) containing the mutant DNA is/are recovered (e.g., by isolating radioactive bands by cutting electroeluting DNA from each slice and recovering the DNA from each by ethanol precipitation).

In an alternative embodiment of the present method, also represented in FIG. 1, DNA in mutant-containing heteroduplexes is visualized without the need for amplification. In this embodiment, a reporter or marker molecule and a device sufficiently sensitive to detect mutants present at the unamplified levels (e.g., at approximately 1 mutant nucleotide sequence in 100,000,000 nonmutant nucleotide sequences) are used. For example, a fluorescent molecule can be used to label the heteroduplex molecules (e.g., by combining denatured or single stranded mutant DNA with an excess of normal or wild type DNA bearing a fluorescent label, under conditions appropriate for formation of heteroduplexes). A scanning separation device in which the emitted light of the fluorophore is made specific by appropriate filters can then be used to detect the fluorescently-labeled mutant-containing heteroduplexes. Alternatively, it is possible to use another charge couple device or other discriminator devices capable of detecting and recording a small number of photons of specific wave number).

The mutant DNA to be resolved by the subject method can be obtained by known techniques from a wide variety of sample types including a mixture of DNA produced by genetic engineering or recombinant DNA method; an animal tissue or body fluid sample; a water sample; or any other DNA-containing material.

In the case in which alteration(s) in a specific gene or DNA region are to be resolved, DNA obtained from a sample to be analyzed is digested with one or more restriction endonucleases whose recognition sequences flank that gene or DNA region. These recognition sequences need not be located precisely at the boundaries of the gene or region.

As described in detail in the Exemplification, the present method has been used to separate mutant sequences created during polymerase-mediated amplification of the human HPRT gene exon 3 sequence from the correctly amplified sequence. As described, exon 3 of the human HPRT gene was amplified using T4 DNA polymerase, modified and unmodified T7 DNA polymerases and Klenow fragment.

Separation of polymerase-induced mutant sequences from correctly amplified sequences was maximized by analyzing the PCR products as heteroduplex mutant-:wild-type sequences using DGGE. Each band isolated from denaturing gradient gels was amplified (using PCR) an additional $10^2$ to $10^3$-fold and separated by another DGGE. Results showed that the present method, in which HPRT exon 3 was amplified using modified T7 DNA polymerase, can successfully detect a mutant fraction of $10^{-3}$ after being amplified a first time and can detect a mutant fraction of $10^{-4}$ after being amplified an additional $10^2$ fold and separated by a second DGGE.

The present invention, in another aspect, relates to a method for determining a mutational spectrum in a DNA sequence of interest present in a population of cells. The term "mutational spectrum", as used herein refers to the compilation of data regarding small alterations in nucleic acid sequence (e.g., point mutations) identified within the DNA sequence of interest. For example assume that a DNA sequence of interest is 100 bp in length, and 4 point mutations are identified within that sequence using the method of the subject invention. Assume further that no single molecule is identified as having more than one point mutation. The mutational spectrum of the 100 base pair region comprises a compilation, or list, of the four mutations which includes the position of the mutation (e.g., nucleotides 1,9,47,63), as well as the specific nucleotide change found to occur at the particular position (e.g. A→G; C→A; T→A; G→C, respectively).

To determine a mutational spectrum, the steps described above for detecting resolution of a mutant DNA species from a non-mutant DNA species are carried out. Following resolution by denaturing gradient gel electrophoresis, gel portions containing labelled heteroduplex bands are excised individually and DNA is purified from the gel material. To determine an individual mutation responsible for the heteroduplex structure, the DNA sequence of the region of interest is determined from the purified DNA. The DNA sequence can be determined by a number of methods, such as the well known dideoxy chain termination method.

By comparing the sequence determined in this manner with the known wild-type (nonmutant) sequence, individual mutations can be characterized. The results of such analysis, when compiled, represent a determination of the mutational spectrum of the DNA sequence of interest. The nonmutant sequence to which the sequence of mutated DNA is compared can be that obtained by analysis of normal (nonmutant) DNA from the individual whose DNA is being assessed. That is, the individual can serve as his or her own reference or control. For example, the mutational spectrum of DNA in cells obtained from a tumor in the individual can be compared with nonmutant DNA from that individual. Alternatively, the information obtained from DNA from an individual, suspected of containing one or more mutations, can be compared with an "established" mutational spectrum. Such an established spectrum is the pattern or profile, previously established by assessing a sufficient number of samples from individuals known to have been exposed to the same genetically toxic substance or event, of mutations known to be associated with the exposure or event for which the individual is being assessed. For example, in the case of an individual with a particular adverse effect (e.g., a liver tumor) thought to be caused by occupational exposure to a particular chemical, the results of analysis of the individual's DNA by the present method (i.e., the individual's mutational spectrum) is compared with the mutational spectrum previously shown to be associated with the exposure of interest. Alternatively, if such an established mutational spectrum is not available, the individual's mutational spectrum can be compared with the mutational spectrum of normal cells of the same type from the individual, grown in the presence of the suspected mutagen and analyzed by the present method.

The method of the present invention is useful as a diagnostic or analytical tool in forensic science in assessing environmental and/or occupational exposures to potentially genetically toxic materials (also referred to as potential mutagens); in biotechnology, particularly in the study of the relationship between the amino acid sequence of enzymes and other biologically-active proteins or protein-containing substances and their respective functions; and in determining the effects of drugs, cosmetics and other chemicals for which toxicity data must be obtained.

USES OF THE PRESENT METHOD

The method of the subject invention can be utilized to determine a mutational spectrum for an individual who has been exposed to chemicals or other conditions suspected of being mutagenic. Such determinations provide information on specific effects of carcinogens. For example, if it is suspected that exposure to a genetically toxic material is the cause of a liver tumor in an individual, it is possible, using the present method, to identify the mutation(s) present in the parenchymal cell population in the individual, to establish the mutational spectrum for that individual and to compare the spectrum with an appropriate reference to determine the relationship between the exposure and the resulting abnormality. It is necessary, in an instance such as this, to know the history of effects (typical effects) of the genetically toxic material(s) on liver cells (e.g., a pre-established mutational spectrum) or to grow normal liver cells from the individual in the presence of the material(s) and determine the resulting mutational spectrum. Comparison with either reference makes it possible to determine the extent of similarity between the reference and the spectrum of the abnormal liver cells from the individual.

It is also possible to determine the mutational spectrum for T cells from an individual having a liver tumor suspected to have been caused by exposure to one or more genetically toxic materials, rather than analyzing liver cells.

In either case, comparison of the spectrum determined for the individual with an appropriate reference will show whether the suspected toxic material did or did not cause a significant number of mutations. A lack of similarities between the two is a clear indication that the suspected material(s) were not causative agents. Consistent presence of a particular spectrum with consistent occurrence or causation of a particular abnormality (e.g., a liver tumor) provides the basis for concluding that the material is a causative agent. The extent to which DNA analysis must be carried out will vary. For example, if there is a well-established spectrum unique to cells exposed to a particular substance, analysis of the corresponding DNA fragment in an individual suspected of being exposed to that substance will provide valuable information on which to assess exposure and its effects. In those cases in which there is no well-established and/or characteristic spectrum, the method of the present invention is used to assess, for example, tumor cells and determine the mutational spectrum; to establish or determine the effects of the suspected toxic material on normal cells (e.g., by exposing and growing normal cells to the material and assessing the mutational spectrum) and; to compare the two to determine causation.

The method of the present invention can be used as a diagnostic tool in forensic; environmental and occupational/occupational health contexts. For example, it can be used to establish the relationship, if any, between exposure to a potentially genetically toxic substance (e.g., in community drinking water or soil, in the workplace, in urban air) and the presence of an abnormality (e.g., tumors, blood dysphagias, etc.). The present method is also useful in testing of chemicals, such as drugs, cosmetics, food additives and pesticides, before they are approved for use by consumers. For example, animals such as rats, mice and rabbits, can be exposed to a new product, such as a food additive and their DNA analyzed by the present method, for mutations. The present method can further be used in the area of biotechnology, such as in the study of the relationship between amino acid sequence and function of enzymes and other biologically active proteins or protein-containing materials.

Another useful aspect of the present invention pertains to the identification of mutations, present within a first mutational spectrum, which result in a selective advantage or disadvantage for cells in which the mutation is present. The identification of such mutations requires mutagenesis of a cell population, followed shortly thereafter by the determination of a first mutational spectrum. The cell population is then expanded by multiple generation growths, followed by a determination of a second mutational spectrum. By comparing the first mutational spectrum with the second mutational spectrum, individual mutations can be identified whose frequency has increased, or decreased, following multiple generation growths.

A requirement of this method for detecting mutations which confer a selective advantage or disadvantage on cells in which they occur, is that the cell population must be suitable for growth in culture. Examples of such cells include mammalian cells which can be grown in culture (e.g., HeLa ... ), other eukaryotic cells which can be maintained in culture (e.g., yeast ... ), and prokaryotic cells (e.g., bacteria).

A variety of mutagens, well known to those skilled in the art, can be used to introduce mutations into DNA. Such mutagens can be introduced into culture medium in an effective amount and duration. Alternatively, purified DNA can be treated with a mutagen, followed by transformation of a suitable cell population. Methods for transformation of eukaryotic and prokaryotic cells are also well known to those skilled in the art.

It is important that the cell population containing mutations be divided into two statistically identical pools, a first pool and a second pool. Shortly after treatment of a cell population with a mutagen, or transformation of a cell population with mutagenized DNA, a first mutational spectrum is determined using the method discussed above. DNA for the first mutational spectrum is isolated from the first pool of cells. The second pool of cells is expanded by multiple generation growths. During this period of clonal expansion, cells which contain a mutation conferring a selective advantage will grow more quickly than cells not containing such a mutation. Consequently, after expansion by multiple generation growths, the percentage of this species of cell in the population of cells will increase. Such an increase will be reflected by a relative increase in the mutant heteroduplex band intensity of the second mutational spectrum autoradiograms, as compared to the mutant heteroduplex band intensity of the first mutational spectrum autoradiograms (assuming that other factors remain constant).

In the converse situation, mutations resulting in a selective disadvantage will be reflected by a relative decrease in the intensity of the mutant heteroduplex band in the autoradiogram of the second mutational spectrum when compared to the autoradiogram of the first mutational spectrum (again, assuming that all other factors remain constant).

In some cases, individual mutations may be lethal in a particular cell type. Such lethal mutations are detectable by the methods of the present invention provided that the mutations are detectable in the first mutational spectrum. Because the first mutational spectrum is determined shortly after mutagenesis, a lethal mutation generally will not have had sufficient time to exert its biological effect (i.e., cell death). Such mutations, therefore, will be represented in the first mutational spectrum. However, following expansion by multiple generation growths, lethal mutations, if present, will result in cell death. In such a case, the autoradiographs of the second mutation spectrum will show no detectable band corresponding to the heteroduplex bands containing a lethal mutation present and detectable in the autoradiographs of the first mutational spectrum.

In another aspect, the present invention pertains to the identification of conditional mutations, present within a first mutational spectrum, which result in a selective advantage or disadvantage for cells in which the mutation is present, under restrictive environmental conditions. The term "conditional mutation", as used herein, refers to a mutation which confers no selective advantage or disadvantage upon cells containing the mutation under certain environmental conditions (termed permissive conditions) but does confer such a selective advantage or disadvantage under certain other environmental conditions (termed restrictive conditions). This aspect of the invention is useful for identifying naturally occurring conditional mutations, or such mutations induced by treatment with mutagenic agents.

To identify conditional mutations, a first mutational spectrum is determined. This first mutational spectrum is determined using DNA isolated from cells which have not been exposed to restrictive conditions. Following the determination of the first mutational spectrum, the population of cells is exposed to restrictive growth conditions followed by multiple generation growths under such restrictive conditions.

A second mutational spectrum is then determined. By comparing autoradiograms from the first and second mutational spectra, individual mutations can be identified whose frequency has increased (selectively advantageous mutants), decreased (selectively disadvantageous mutants), or is undetectable (lethal mutants) following multiple generation growths under restrictive conditions.

The skilled artisan is familiar with growth parameters which can be altered to create restrictive or permissive conditions. Such parameters include increased or decreased temperature, osmolarity, or pH. Growth in deuterium-containing media is another parameter which can be adjusted.

The methods of this invention are also useful for identifying functional domains within a protein of interest which are sensitive to mutational perturbation. The identification of such functional domains can lead to rational approaches to protein engineering. Additionally, the methods are useful for identifying regulatory sequences within a gene which are sensitive to mutational events. For example, promoter mutations which result in the termination of transcription of mRNA encoding an essential cellular protein, can be identified.

The present invention will now be illustrated by the following Exemplification, which is not to be seen as limiting in any way.

EXEMPLIFICATION

MATERIALS AND METHODS

Materials

T4 and Taq DNA polymerases were obtained from New England Biolabs (Beverly, MA); Klenow fragment of *E. coli* DNA polymerase I from Bethesda Research Laboratories (Gaithersburg, MD); and modified T7 DNA polymerase (or Sequenase TM) from US Biochemicals (Cleveland, OH). T7 DNA polymerase (unmodified) and 2'-deoxynucleoside 5'-triphosphates as 100 mM solutions were obtained from Pharmacia (Piscataway, NJ). The oligonucleotides (Synthetic Genetics, CA) used as primers for PCR were the following: for HPRT exon 3:
  primer P1: 5'-CATATATTAAATATACTCAC-3'
  primer P2: 5'-TCCTGATTTTATTTCTGTAG-3'
  primer P3: 5'-GACTGAACGTCTTGCTCGAG-3'for human mitochondrial fragment (299-bp):
  primer P4: 5'-GATACTGGCATTTTGTAGAT-3'
  primer P5: 5'-GAATTTTATGGAGAAAGGGA-3'for human 45s rRNA fragment (135-bp):
  primer P6: 5'-TAGCCGGGTCACCGGTAGGC-3'
  primer P7: 5'-GGGGAGGTATATCTTTCGCT-3'

To obtain end-labeled fragments, the amplification was carried out using 5'-end-labeled primers (specific activity:150Ci/mmole) using [$\gamma$-P$^{32}$]ATP (7000Ci/mmole, New England Nuclear), T4 polynucleotide kinase, and the reagents in the 5' end DNA terminus labeling system (Bethesda Research Laboratories).

Genomic DNA was isolated from exponentially growing male TK6 human lymphoblasts; (Skopek, T. R. et al., *Biochem. Biophys. Res. Commun.* 84:411.416 (1978)), according to the method described by Porteous, (*Somat. Cell Mol. Genet.* 11:445.454 (1985)). In this study, the 184-bp exon 3 sequence of the X-linked HPRT gene was used as template because it contains naturally occurring high and low temperature melting domains of 84-bp and 100-bp, respectively (FIG. 1).

METHODS

The PCR conditions used for T4 DNA polymerase (Keohavong, P. et al., *DNA* 7:63–70 (1988)), and for both the modified and unmodified T7 DNA polymerases (Keohavong, P. et al., *Gene* 71:211–216 (1988)) were similar to those described for Klenow fragment (Saiki et al., *Science* 230:1350–1354 (1985); (Mullis et al., *Meth. in Enzymol.* 155:335–350 (1987)). A 100 µl reaction mixture contained: DNA templates (5 µg of genomic DNA or PCR products after gel purification), 10 mM Tris HCl (pH 8.0), 5 mM MgCl$_2$, 2.7 mM of each dNTP (2.15 mM for T4 DNA polymerase). 3µM of each primer and, for T4 DNA polymerase, 5% DMSO (vol/vol). Each amplification cycle consisted of: (1) boiling the reaction mixture 1 min, (2) primer-template hybridization 1 min at 37° C., (3) addition of 0.5 unit of T4 DNA polymerase or 2 units of modified and unmodified T7 DNA polymerases and 2 min incubation at 37° C.

The conditions for experiments with Klenow fragment were exactly as described in the original method. The conditions for Taq DNA polymerase (New England Biolabs) were as follows: a 100 µl reaction mixture contained: 16.6 mM (NH$_4$)$_2$SO$_4$, 67 mM Tris-HCl (pH 8.8 at 25° C.), 6.7 mM MgCl$_2$, 10 mM βME, 200 µM of each of the four dNTPs and 1 µM of each primer. Each amplification cycle consisted of heating the reaction mixture at 93° C. for 1 min (except 3 min for the first cycle), primer-template hybridization at 53° C. for 2 min, and DNA chain synthesis at 70° C. for 2 min. One µl (2.5 units) of Taq DNA polymerase was added every 10 cycles following the 2 min incubation at 53° C.

To maximize the separation of polymerase induced mutant sequences from the correctly amplified sequences, the PCR products were analyzed as heteroduplex mutant: wild type sequences. $5 \times 10^4$ to $5 \times 10^5$ cpm of the amplified DNA were diluted in 30 μl of 400 mM NaCl, 10 mM Tris HCl pH 7.5, 2mM EDTA, boiled 5 min, and allowed to anneal at 65° C. for 5 h. The DNA was recovered by ethanol precipitation and electrophoresed on a 12.5% polyacrylamide gel (bis/acryl=1/37.5) containing a linearly increasing gradient of denaturant from 15% (vol/vol) to 30% (vol/vol) (100% denaturant=7M urea and 40% formamide) (myers, R. M. et al., Methods Enzymol. 155:501-527 (1987)). The gel was run for 15h at 150V, submerged in 60° C. TAE buffer (40 mM Tris HCl, 20mM NaOAc, 1 mM EDTA pH 8.3). The gel was then fixed in 40% methanol and 5% glycerol, dried, and autoradiographed.

The gel was dried without fixation with methanol. Radioactive bands were first located by autoradiography and excised through the autoradiogram superimposed on the gel. The DNA was electroeluted from the gel slices and recovered by ethanol precipitation.

2. RESULTS

Figure 2A:
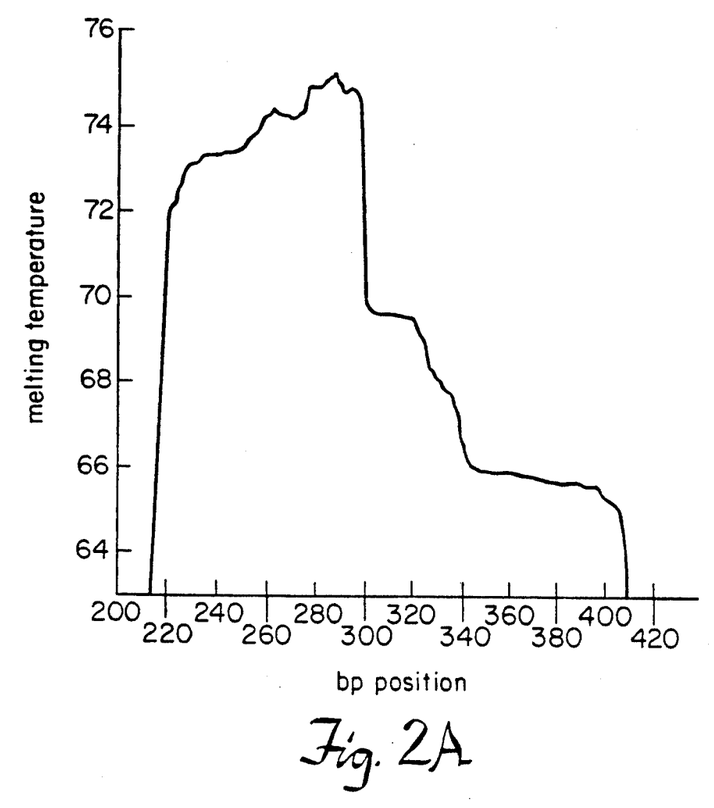
Figure 2B:
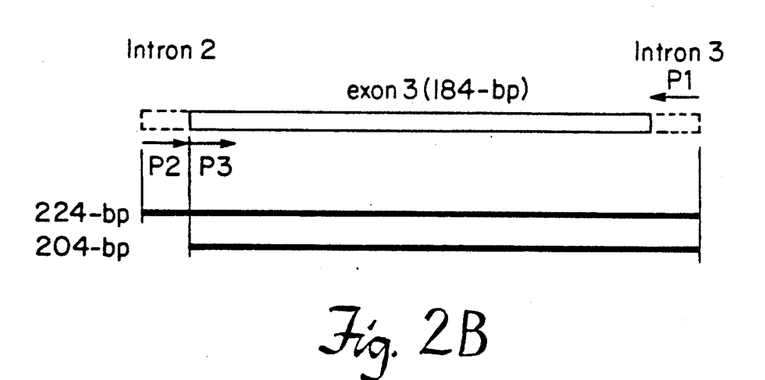

The DNA amplification was carried out from genomic DNA using primers P1 and P2 which immediately flanked the human HPRT exon 3 sequence (FIG. 1B) and the following five DNA polymerases: T4, modified and unmodified T7, Klenow fragment of Pol I, and Taq. The efficiency of amplification of the expected-size 224-bp fragment varied according to the type of the DNA polymerase. Efficiency was estimated according to the equation:

$$(1+Y)^N = \text{fold amplification}.$$

where Y is the efficiency per cycle and N is the number of cycles performed (Saiki, R.K. et al., Science 230:1350-1354 (1985)). Efficiencies during the first 20 cycles were estimated to be 90-93% with either modified or unmodified T7 DNA polymerases, 88% with Klenow fragment and Taq DNA polymerase. T4 DNA polymerase gave an efficiency of 60%, through 30 cycles. In addition to the expected-size 224-bp fragment, unwanted sequences appeared, especially when using Klenow fragment. The efficiency and yield of amplification using modified T7 DNA polymerase was exceptional. 30 cycles yielded more than $4 \times 10^7$ fold amplification. The high efficiency obtained with modified T7 DNA polymerase probably resulted from its highly processive activity (Tabor, S. et al., J. Biol. Chem. 262:16212-16223 (1987)); (Tabor, S. et al., Proc. Natl. Acad. Sci. USA 84:4767-4771 (1987)). This enzyme has also been used to amplify several other sequences directly from human cells including a 299-bp fragment from the mitochondrial genome (Anderson, S. et al., Nature 290:457-465 (1981)) (FIG. 2B, part 1) and a 135-bp fragment from 45S ribosomal RNA genes (Schmickel. R.D. Pediat. Res. 7:5 (1973)). Furthermore, these fragments and the 224-bp exon 3 fragment were able to be simultaneously amplified in the same reaction mixture containing the three independent pairs of primers.

The 184-bp exon 3 sequence is composed of 84-bp of high temperature melting domain and 100-bp of low temperature melting domain (FIG. 1). Base-pair substitutions and small frameshift mutations throughout the low temperature melting domain of this sequence have been shown to be separable from the wild type by DGGE when first converted into heteroduplex mutant-:wild type sequences. To analyze the fidelity of DNA lification by DGGE, the PCR products were first boiled and reannealed so that each strand of the mutant homoduplexes was hybridized to the complementary strand of the correctly amplified sequences (wild type) present in excess. In this manner, each mutant sequence was expected to be detected as two heteroduplexes, which would separate further from the wild type than the mutant homoduplex (Myers, R.M. et al., Cold Spring Harbor Symp. Quant. Biol. 51:275-283 (1986); Tabor, S. et al., Proc. Natl. Acad. Sci. USA 84:4767-4771 (1987)). When the exon 3 sequence was separated by DGGE after $10^6$ and $10^8$ fold amplification for each DNA polymerase, the wild type sequence focused at 24% of denaturant concentrations, and, in addition, a series of bands were observed in lower denaturant concentrations. After $10^8$ fold amplification (FIG. 3), the number of such bands varied from three with T4 DNA polymerase to more than a dozen with Klenow fragment and Taq DNA polymerase. The individual bands each represented between 1 and 3% of the total radioactive DNA analyzed on the gel. Three distinct patterns of mutant bands appeared: (a) with T4 DNA polymerase, (b) with Taq DNA polymerase, (c) with modified or unmodified T7 DNA polymerases. The pattern produced by Klenow fragment, apart from three bands, was identical to that observed with the two T7 DNA polymerases. This suggests that both the modified and unmodified T7 DNA polymerases and also Klenow fragment generated mutations of similar kinds and positions while copying the low temperature melting domain of exon 3.

The fraction of radioactivity separated as bands by DGGE was estimated by densitometry through comparison of the intensity of the putative mutant sequences relative to that of the wild type. The densitometric scanning yielded an integral total absorbance for the wild type peak and putative mutant heteroduplex region between the wild type peak and the origin of the gel. Background events such as depurination within homoduplexes were accounted by eluting radioactive DNA from a wild type peak. The DNA was boiled, annealed, and separated by DGGE. This background fraction, totaling about 4%, was subtracted from the putative heteroduplex fraction. Thus, the PCR-related mutant fraction (MF) was estimated as:

$$MF = (\text{absorbance in heteroduplex region} - \text{background absorbance})(\tfrac{1}{2})/(\text{total absorbance}).$$

The MF at $10^6$ and $10^8$ fold amplification were found to be 0.25% and 1.5% for T4; 3.7% and 4.5% for modified T7; 3.8% and 4.7% for unmodified T7; 11% and 16% for Klenow fragment; and 31% and 33% for Taq DNA polymerases.

The error rate (f) for each DNA polymerase was then estimated according to the equation:

$$MF = b \times f \times d$$

where b is the number of nucleotides synthesized on both strands of the template for which mutants would be detected ($2 \times 100$ nucleotides for the low temperature melting domain of exon 3) and d is the number of duplications ($10^6$ and $10^8$ fold amplification represented 20 and 26 duplications, respectively). The error rates (mutations/base/duplication), f, for $10^6$ and $10^8$ fold amplification were found to be 0.6 and 3 ($\times 10^{-6}$) for T4; 9.0 and 8.5 ($\times 10^{-6}$) for modified T7; 9.5 and 9.0 ($\times 10^{-6}$) for unmodified T7; 3 ($\times 10^{-5}$) for Klenow fragment; and 7.5 and 6.5 ($\times 10^{-5}$) for Taq DNA polymerases.

Each individual band isolated from denaturing gradient gels was amplified an additional $10^2$ to $10^3$ fold and separated by another DGGE. In the case of the bands 3 and 4 generated by T4 DNA polymerase, this process resulted in two major homoduplexes, mutant and wild type. After boiling and annealing, these same DNA gave rise to two additional bands, expected to correspond to the mutant:wild type heteroduplexes. The fact that both bands gave rise to precisely the same pattern of bands after boiling and annealing was consistent with the interpretation that they were heteroduplexes formed from the opposite strands of the same mutant homoduplex. Sequence analysis of these mutant homoduplexes showed a G-C to A-T substitution at position 351 (see Table 1). Two less intense bands created by T4 DNA polymerase and 14 of the most intense bands created by Taq DNA polymerase were isolated and sequenced in the same manner. Some of these sequences did not yield homoduplexes sufficiently separated from the wild type by DGGE for isolation and, in this case, sequencing was carried out using the heteroduplexes. The kinds and positions of the most frequent mutations found for T4 and Taq DNA polymerases are summarized in Table 1. All of the mutations determined were found to be base-pair substitutions. The three mutations induced by T4 DNA polymerase were G-C to A-T transitions. Seven mutations appearing with Taq DNA polymerase were found to be A-T to G-C transitions. No additions or deletions were detected among the mutations determined. These data showed that T4 and Taq DNA polymerases catalyzed the PCR differently with regard to the kinds of mutations induced in the low temperature melting domain of exon 3. T4 DNA polymerase induced a single "hot spot" G-C to A-T transition and Taq DNA polymerase induced at least seven different A-T to G-C transitions among the 32 A-T base-pairs in the low temperature melting domain of exon 3.

TABLE 1

| Mutations generated by T4 and Taq DNA polymerases | | | |
|---|---|---|---|
| DNA polymerases | kinds of mutations | bands number | *positions |
| T4 | G—C to A—T | 1 | 319 |
| | | 2 | 320 |
| | | 3 and 4 | 351 |
| Taq | A—T to G—C | 5 | 337 |
| | | 6 | 399 |
| | | 7 | 334 |
| | | 8 | 333 |
| | | 9 | 371 |
| | | 10 | 358 |
| | | 11 | 393 |

*the positions of the mutations in the low temperature melting domain of exon 3 were numbered starting from the 5' end of the human HPRT cDNA (Patel et al., Somat. Cell. Mol. Genet. 10:483-493 (1984)).

The background of the polymerase-induced mutations is a limiting factor for detecting pre-existing mutants present as a small number of copies in cell populations. In order to probe this limit. HPRT exon 3 was amplified using modified T7 DNA polymerase from samples of HPRT wild type cells (Skopek, T.R. et al., Biochem. Biophys. Res. Commun. 84:411-416 (1978)); containing known fractions of exon 3 mutant cells, HPRT-Munich (Cariello, N.F. et al., Am. J. Hum. Genet. 42:726-734 (1988)). Analysis by DGGE showed that a mutant fraction of $10^{-3}$ can be detected. To further increase the sensitivity of the protocol, the heteroduplex region between the wild type band and the origin of the gel was excised, the DNA was isolated and amplified an additional $10^2$ fold. After separation by a second DGGE, one of the wild type:HPRT-Munich heteroduplexes present at a mutant fraction of $10^{-4}$ was observed. By comparison with this heteroduplex band, the most prominent mutant sequences induced by modified T7 DNA polymerase corresponded to mutant fractions of about $2 \times 10^{-4}$.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:
1. A method for determining a mutational spectrum in a DNA sequence of interest present in a population of cells comprising the steps of:
   (a) providing fragmented double-stranded DNA, which is a mixture of mutant DNA-containing fragments and nonmutant DNA-containing fragments;
   (b) separating the fragmented double-stranded DNA on the basis of molecular weight and isolating the DNA sequence of interest;
   (c) denaturing a annealing the DNA sequence of interest under conditions appropriate for heteroduplex formation;
   (d) separating the products of step c) by denaturing gradient gel electrophoresis thereby resolving heteroduplex molecules and homoduplex molecules, and isolating the heteroduplex molecules from the denaturing gradient gel;
   (e) amplifying the isolated heteroduplex molecules from step d) by polymerase chain reaction under conditions appropriate for polymerization with an error rate of about $10^{-5}$ errors per base pair or less to produce a quantity of DNA sufficient for detection following denaturing gradient gel electrophoresis;
   (f) denaturing and reannealing the products of step e) under conditions appropriate for heteroduplex formation, each heteroduplex containing a mutant DNA sequence, and separating the products by denaturing gradient gel electrophoresis;
   (g) isolating and amplifying separately DNA in each band produced in step f), by polymerase chain reaction under conditions appropriate for polymerization with an error rate of about $10^{-5}$ errors per base pair or less;
   (h) determining the nucleotide sequence of DNA from each band after amplification in step g); and
   (i) comparing the nucleotide sequence of each band with the nucleotide sequence of corresponding nonmutant DNA to determine the difference in each.

2. A method of claim 1 wherein the mutant DNA sequence is present at a mutational frequency of from 1 to about $1 \times 10^{-8}$.

3. A method of claim 2 wherein the cell population is a human cell population.

4. A method for determining a mutational spectrum in a DNA sequence of interest present in a population of cells from an individual exposed to a suspected mutagen comprising the steps of:
   (a) isolating DNA from the population of cells;
   (b) digesting the isolated DNA with one or more appropriately-selected restriction endonucleases, to produce a mixture of DNA fragments, the fragments comprising a mixture of mutant DNA-containing and nonmutant DNA-containing fragments;

(c) separating the mixture of DNA fragments on the basis of molecular weight, and isolating the DNA sequence of interest;

(d) denaturing and annealing the DNA sequence of interest under conditions appropriate for heteroduplex formation;

(e) separating mutant-containing heteroduplexes from nonmutant-containing homoduplexes by denaturing gradient gel electrophoresis and isolating the heteroduplex fraction;

(f) amplifying the mutant-containing heteroduplexes by polymerase chain reaction under conditions appropriate for polymerization with an error rate of about $10^{-5}$ errors per base pair or less;

(g) denaturing and annealing the products of step (f) under conditions appropriate for heteroduplex formation;

(h) separating mutant-containing heteroduplexes from nonmutant-containing homoduplexes by denaturing gradient gel electrophoresis to produce for each heteroduplex a band with a characteristic location on the denaturing gradient gel;

(i) determining the nucleotide sequence of DNA from each band formed in step (h); and (j) comparing the nucleotide sequence of DNA from each band with the nucleotide sequence of corresponding nonmutant DNA to determine the mutations in each.

5. A method for detecting the presence of a mutation in a DNA sequence of interest present in a population of cells, comprising the steps of:

(a) providing fragmented double-stranded DNA, which is a mixture of mutant DNA-containing fragments and nonmutant DNA-containing fragments;

(b) separating the fragmented double-stranded DNA from step a) on the basis of molecular weight and isolating the DNA sequence of interest;

(c) denaturing and annealing the isolated DNA sequence of interest from step b) under conditions appropriate for heteroduplex formation;

(d) separating the products of step c) by denaturing gradient gel electrophoresis thereby resolving heteroduplex from homoduplex molecules, and isolating the heteroduplex molecules form the denaturing gradient gel;

(e) amplifying the isolated heteroduplex molecules from step d) by polymerase chain reaction under conditions appropriate for polymerization with an error rate of about $10^{-5}$ errors per base pair or less to produce a quantity of DNA sufficient for detection following denaturing gradient gel electrophoresis;

(f) denaturing and annealing the amplification product of step e) under conditions appropriate for heteroduplex formation; and (g) separating the products of step f) by denaturing gradient gel electrophoresis to detect heteroduplex bands which are indicative of the presence of mutations in the DNA sequence.

6. A method of claim 5, wherein the mutant DNA-containing fragment is present at a mutational frequency of from 1 to about $10^{-8}$.

7. A method of claim 5, wherein the mixture of mutant DNA-containing fragments are of human origin.

* * * * *